United States Patent [19]
Hendrickson et al.

[11] Patent Number: 6,125,848
[45] Date of Patent: Oct. 3, 2000

[54] DISTAL VOLUME MONITORING

[75] Inventors: Carl H. Hendrickson, Madison; Ronald L. Tobia, Sun Prairie; Kevin G. Tissot, Brooklyn, all of Wis.

[73] Assignee: Datex-Ohmeda, Inc., Madison, Wis.

[21] Appl. No.: 08/938,850

[22] Filed: Sep. 26, 1997

[51] Int. Cl.$^7$ .................................................. A61M 16/00
[52] U.S. Cl. ................................ 128/204.22; 128/204.23
[58] Field of Search ........................ 128/204.22, 204.23, 128/204.21, 204.26, 203.12, 203.25, 205.23, 911; 600/538, 540

[56] References Cited

U.S. PATENT DOCUMENTS

| | | | |
|---|---|---|---|
| 3,856,051 | 12/1974 | Bain | 138/114 |
| 3,910,261 | 10/1975 | Ragsdale et al. | 128/207 |
| 5,107,831 | 4/1992 | Halpern et al. | 128/204.26 |
| 5,121,746 | 6/1992 | Sikora | 128/203.12 |
| 5,660,171 | 8/1997 | Kimm et al. | 128/204.23 |

*Primary Examiner*—Aaron J. Lewis
*Assistant Examiner*—Teena K Mitchell
*Attorney, Agent, or Firm*—Andrus, Sceales, Starke & Sawall

[57] ABSTRACT

A system that enables the accurate monitoring of tidal volume of a patient when using a Bain, Mapleson D or similar type of patient breathing circuit in an anesthesia system. The system allows the use of flow sensors positioned at the machine or distal end of the patient breathing circuit and not at the less desirable patient or proximal end of the patient breathing circuit. Thus, the flow sensors can be positioned out of the way of the patient and will provide a measurement of the tidal volume of the patient. A CPU is used to take into account, the additional fresh gas provided to the patient breathing circuit during the expiration cycle to correct the flow monitored in the main breathing tube that supplies the gas to the patient from a ventilator or breathing bag.

14 Claims, 1 Drawing Sheet

DISTAL VOLUME MONITORING

BACKGROUND

The present invention relates to the monitoring of volume to a patient during anesthesia, and more particularly, to a system that allows the monitoring of the tidal volume to the patient by the use of flow sensors that are located at the machine or distal end of the patient breathing circuit.

In general, anesthesia systems are utilized in operating rooms and comprise various equipment necessary to anesthetize the patient and maintain the patient in that state until the operation is completed and it is possible to terminate the introduction of the anesthetic agent. Such systems include various pressure regulators, flow control devices, gas mixing devices and vaporizers to provide an anesthetic laden stream of gas to the patient. The patient is connected to the system by means of a face mask or other device and which interfaces with the anesthesia system by means of a patient breathing circuit. The system provides the anesthetic laden gas to the patient during an inspiratory cycle and receives the patient's exhaled gases during an expiratory cycle.

With current anesthesia machines, it is important to monitor the tidal volume of such gas administered to that patient. The present systems provide one or more flow sensors that monitor flow at various times through the patient breathing circuit and then integrate that flow with respect to a specific time to arrive at the tidal volume. In many such systems, the flow sensor that monitors the flow is located in the expiration side of the breathing circuit and the expiration cycle time is used to determine the tidal volume.

With the standard circle system breathing circuit, the flow sensor or flow sensors are conveniently located at the distal end of the patient breathing circuit in the inspiratory or expiratory limbs, that is, the end of the patient breathing circuit that is affixed to the anesthesia machine. Such position is convenient and is possible due to the path of flow within the circle breathing system since it is basically a closed system and the flow of gas follows the direction of a circle with fresh gas added to the system.

As used herein, the distal end of a patent breathing circuit is considered to be the end of the patient breathing circuit that is attached to the anesthesia machine and the proximal end of the patient breathing circuit is considered to be that end that is attached to the patient administration device, that is the face mask, endotracheal tube or the like.

A problem arises, however, with the use of a Bain breathing circuit or Mapleson D circuit where a large central tube connects the anesthesia machine with the patient and there is a continual to-fro pattern of flow within that tube. As such, the patient basically rebreathes some of the exhaled gas from the large central tube while receiving fresh gas through a separate tube that either lies coaxially within the large central tube as in the Bain circuit or through a separate tube that is outside but parallels the large central tube (Mapleson D circuit), both of which introduce the fresh gas to the system at or near the proximal end of the large central tube. Accordingly, if the tidal volume is measured at the distal end of such circuit, the reading will be inaccurate since the fresh gas flow continues, even during expiration and the flow sensor in the expiratory gas stream will read that additional fresh gas flow administered during the expiratory cycle and thus will read a flow of gas that is not actually administered to the patient.

In such cases, the flow sensor must, therefore, be positioned at the proximal end of the patient breathing circuit, that is, at the end of the circuit that is connected to the patient so that it reads only the gases actually exhaled by the patient. The difficulty with such arrangement is that such circuits are commonly used for infants and the positioning of the flow sensor at the end of the patient circuit connected to the patient adds additional and undesirable dead space to the circuit and further adds additional bulk to a device that is affixed to the patient.

Further, the location of the flow sensor adjacent the patient also introduces additional connections into the patient breathing circuit at a point where accidental disconnects frequently occur. Each additional connection at the proximal end of the circuit increases the possibility of leakage or disconnection.

As further problem of having the flow sensor at the patient connection is the additional clutter to the overall patient breathing circuit and the access to the patient. Often, the Bain circuit is used for facial surgery since the single tube reduces the clutter and enhances the access to the patient's face. By adding the proximal sensor with the added tubing, wiring and the like the additional clutter makes facial operations that much more difficult to perform.

Accordingly, it would be advantageous to carry out the monitoring of the tidal volume of the patient at the distal end of the patient circuit even when the circuit is of the type that is of the Bain and Mapleson D circuit type with a large tube to the patient with the fresh gas provided by a separate tubing to that patient.

SUMMARY OF THE INVENTION

In accordance with the present invention, a system is provided that carries out the monitoring of the tidal volume of gas delivered to the patient through a Bain or Mapleson D circuit or similar circuit and which accurately carries out the monitoring of flow expired from the patient at the machine end or distal end of the patient breathing circuit.

In carrying out the present invention, a further flow sensor is used, also at the distal end of the patient circuit and which monitors the flow in the fresh gas delivered to the patient during the expiratory phase of the ventilation cycle. Alternatively, the fresh gas flow information may also be obtained from an electronic mixer or by direct input by the user. A processor obtains the data representative of the total expired flow from the patient from a sensor located at the machine end of the patient breathing circuit and also receives the information as to the flow of fresh gas during the expiratory cycle and carries out a subtraction step that reduces the total flow sensed by the flow of the fresh gas during expiration and thus calculates an accurate value of the flow for the patient's expiration. That value, when integrated with respect to the appropriate time during expiration, provides an accurate determination of the patient's tidal volume without having a flow sensor at or near the patient connection.

As a further use of the flow sensor in the fresh gas stream, an accurate determination can be made of the fresh gas flow during the inspiratory cycle to obtain total gas delivered to the patient for purposes as determining volume apnea. In such case, the flow in the fresh gas stream can be monitored during the inspiratory cycle can be added to the flow of gas in the main patient breathing circuit also during the inspiratory cycle and determine total flow of gas to the patient.

DETAILED DESCRIPTION OF THE INVENTION

Figure 1:
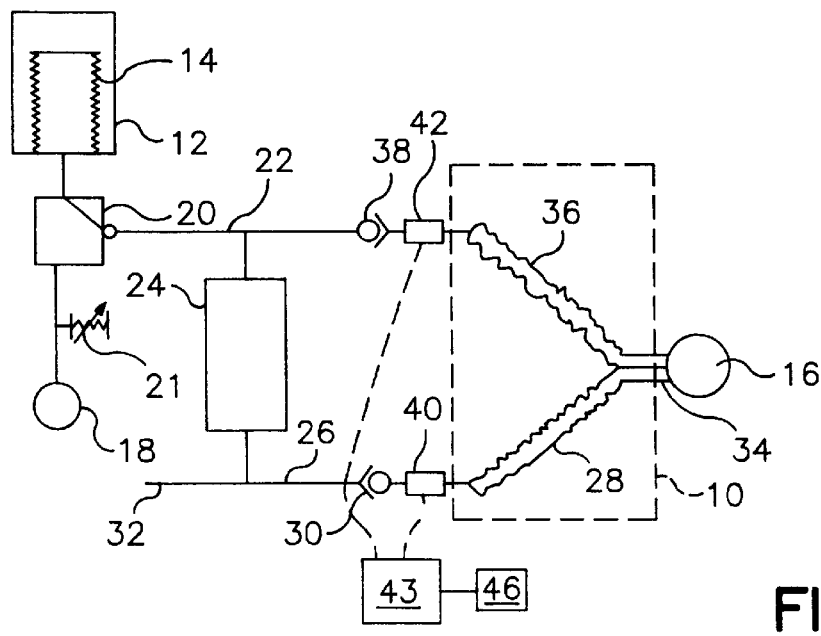
FIG. 1 is schematic view of a circle patient breathing circuit showing the typical location of the flow sensors used to determine tidal volume.

Referring now to FIG. 1, there is shown a schematic view of a typical circle patient breathing circuit 10. As is conventional in that circuit, a bellows container 12 encloses a collapsible bellows 14 that provides a positive breath to the patient. As is known, however, a ventilator (not shown) forces a controlled amount of a gas into the bellows container 12 to collapse the bellows 14 to force the breathing gas to the patient 16. Alternatively, a flexible bag 18 may be used by the clinician so as to manually squeeze the bag and provide that breathing gas to the patient 16 during anesthesia. In either case, there is period that gas is being supplied to the patient, that is, the inspiratory cycle, and a period that the patient is exhaling back into the breathing circuit, that is, the expiratory cycle.

A bag to ventilator switch 20 allows the clinician to select the mode of delivering that breathing gas, i.e. through use of the powered ventilator or by the manual bagging mode. An adjustable pressure limiting valve 21 is also provided that releases gas from the system when a predetermined pressure is exceeded.

In either case, the breathing gas progresses in conduit 22 where it passes through an absorber 24 where the $CO_2$ from the patient's exhalation is removed and the breathing gas continues through an inlet conduit 26 to the inspiratory limb 28 of the circle patient breathing circuit 10. That gas passes through a check valve 30 to assure the direction of the flow is in the correct direction and a fresh gas inlet 32 is also provided to add the fresh gas to the system and which combines with the gas circulating in conduit 26 to the circle patient breathing circuit 10 to be administered to the patient.

A patient connection 34 connects to the patient 16 and provides that breathing gas to the patient 16. As the patient exhales, the gas passes through an expiratory limb 36 of the circle patient breathing circuit 10 and passes that exhaled gas through another check valve 38 to be continuously recirculated through the circle patient breathing circuit 10.

An inspiratory flow sensor 40 is provided to monitor the flow in the inspiratory limb 28 and an expiratory flow sensor 42 likewise monitors the flow in the expiratory limb 36. In some systems, only one flow sensor may be used to determine the flow in patient circuit and generally, an expiratory flow sensor monitors the flow from the patient and that flow signal is integrated with respect to the time of the expiratory cycle. That integration may be processed by a CPU 43 to arrive at the tidal volume of the gas to the patient 16 and which may be displayed to the clinician at a display 46.

Figure 2:
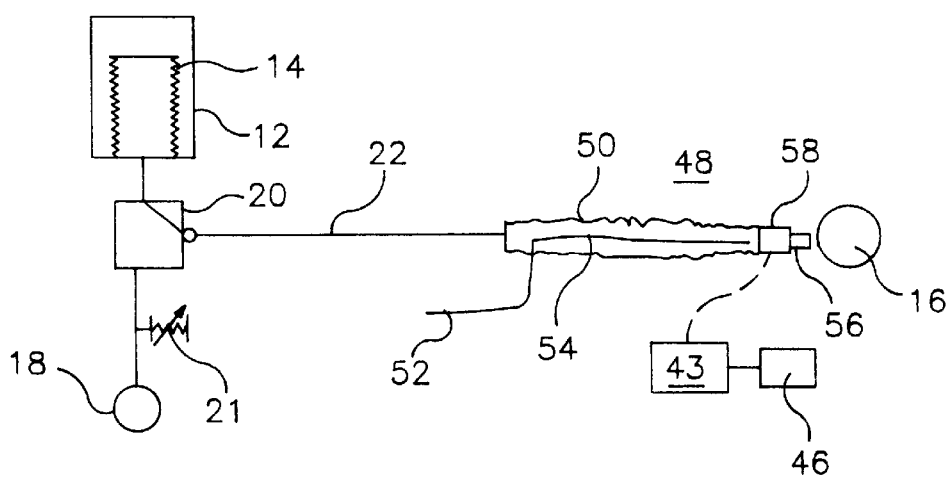
FIG. 2 is a schematic view of a Bain circuit showing the proximal flow sensor typically used with that breathing circuit.
Figure 3:
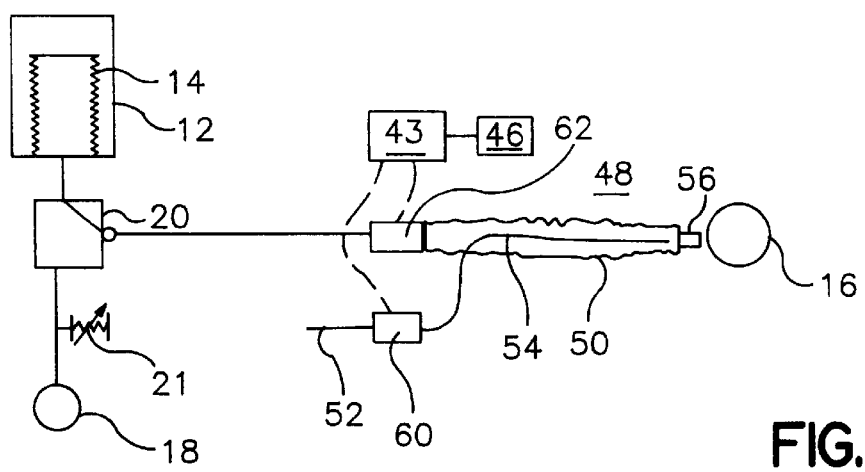
FIG. 3 is a schematic view of a Bain patient breathing circuit showing the location and use of flow sensors used to carry out the present invention.

Turning now to FIG. 2, there is shown a schematic view of a conventional Bain patient breathing circuit 48. The Bain patient breathing circuit 48 comprises some of the same machine components as the circle patient breathing circuit 10 of FIG. 1 and, where applicable, the same numbers have been assigned to those components. The difference is in the Bain patient breathing circuit 48 being comprised of a large bore tube 50 that receives the breathing gas from the bellows 14 or the flexible bag 18 for delivery to the patient. As can be seen, the fresh gas is provided at a fresh gas inlet 52 and which is then carried in a smaller tubing 54 that is located internal and coaxial to the large bore tube 50 and terminates adjacent the patient connector 56. As can thus be seen, as the patient exhales and inhales, the breathing gas moves to and fro within the large bore tube 50 and the patient inhales some of the gas from the large bore tube 50 and fresh gas is provided continuously by the small tubing 54 to the patient 16. Accordingly, to determine the tidal volume, a flow sensor 58 is located at the proximal or patient end of the Bain patient breathing circuit 48 to monitor all of the patients expired gas. If a flow sensor is placed at the distal or machine end of Bain patient breathing circuit 48, it would read high since it would also include the effect of fresh gas that is delivered continuously and therefore would monitor the fresh gas that is provided even during the expiration cycle. That fresh gas has, of course, not been inhaled by the patient so that the flow sensor at the distal or machine end would provide an inaccurate indication of tidal volume to the patient.

As can also be seen, with the placement of the flow sensor 58 at the proximal end of the Bain patient breathing circuit 48, the device adds considerable additional dead space to the overall breathing system and also adds clutter to the patient connector, thereby making facial surgery more difficult. The additional dead space is of utmost importance when dealing with pediatric or small infant patients where the flows are considerably small. It should be noted that the Mapleson D circuit that is commonly used in patient breathing circuits is very similar to the Bain patient breathing circuit but the small tubing 54 is located external of the large bore tube 50 and runs along that exterior surface and introduces the fresh gas through the patient connector.

Finally, turning now to FIG,. 3, there is shown a schematic view of a patient breathing circuit having flow sensors located in accordance with the present invention. Again, as may be seen, the Bain patient breathing circuit 48 is used as in FIG. 2. In this case, however, a fresh gas flow sensor 60 has been positioned in the fresh gas inlet 52 and which thereby monitors the flow of fresh gas to the Bain breathing circuit at all times. A further flow sensor 62 is positioned so as to monitor the flow in the large bore tube 50 and which, therefore can monitor the flow from the patient expiration during that cycle. As noted, both of the flow sensors 60 and 62 are positioned at the distal end of the Bain patient breathing circuit 48.

Thus the CPU 43 can receive a signal representative of flow of fresh gas to the Bain patient breathing circuit 48 during the patient expiration period and also receive a signal representative of the flow of the gases from the patient at the machine or proximal end of the large bore tube 50. The CPU 43 can thus subtract the flow in the fresh gas conduit during that expiration period and from the total flow of gas from the patient during the expiration and arrive at an accurate determination of the flow from the patient, having taken into account, the flow that was introduced during the expiration cycle and which was not inhaled by the patient. As noted, the information as to the fresh gas flow can be manually obtained from a user input or directly from an electronic mixer.

Accordingly, by integrating that value of flow, an accurate determination of tidal volume can be obtained without having a flow sensor located at the patient or proximal end of the Bain patient breathing circuit.

While the present invention has been set forth in terms of a specific embodiment, it will be understood that the monitoring system herein disclosed may be modified or altered by the those skilled in the art to other configurations.

Accordingly, the invention is to be broadly construed and limited only by the scope and spirit of the claims appended hereto.

We claim:

1. A system for determining the tidal volume of a patient undergoing anesthesia, said system comprising a breathing means, including a source of anesthesia, to supply breaths to a patient during an inspiratory cycle and to allow a patient to exhale during an expiratory cycle, a patient breathing circuit having a main delivery tube having a distal end for connection to the breathing means and a proximal end for connection to a patient connector in communication with a patient, the main delivery tube communicating between said breathing means and a patient, a source of fresh gas, a tubing for delivering the fresh gas from said source of fresh gas to the patient connector for delivery to a patient, means to determine the flow of gas within said main delivery tube, means to determine the flow of fresh gas in said tubing during said expiratory cycle, a processor for receiving signals from said means to determine the fresh gas flow in said tubing and the flow of gas in said main delivery tube to provide an accurate measurement of the volume of gas expired by a patient.

2. The system for determining the tidal volume of a patient undergoing anesthesia as defined in claim 1 wherein said patient breathing circuit is a Bain circuit.

3. The system for determining the tidal volume of a patient undergoing anesthesia as defined in claim 1 wherein said patient breathing circuit is a Mapleson D circuit.

4. The system for determining the tidal volume of a patient undergoing anesthesia as defined in claim 1 wherein said breathing means is a ventilator.

5. A system for determining the tidal volume of a patient receiving breaths from a breathing means during an inspiratory cycle for receiving exhalation from a patient during an expiratory cycle, said system comprising a patient breathing circuit having a main delivery tube having a distal end for connecting to a breathing means and a proximal end for connecting to a patient and communicating between the breathing means and a patient, a source of fresh gas, a tubing for delivering fresh gas from said source of fresh gas to the main delivery tube between its distal and proximal ends for delivery to a patient, a first flow sensor to determine the flow of gas within said main delivery tube, a second flow sensor to determine the flow of fresh gas in said tubing during said expiratory cycle, a processor for receiving signals from said first and second flow monitors to provide an accurate measurement of the volume of gas expired by a patient.

6. The system for determining the tidal volume of a patient as defined in claim 5 wherein said first flow sensor is located at the distal end of said main delivery tube.

7. The system for determining the tidal volume of a patient as defined in claim 5 wherein said fresh gas tubing has a proximal end providing the fresh gas to a patient at or near the proximal end of said main delivery tube and a distal end an wherein said second flow sensor is located at the distal end of said fresh gas tubing.

8. The system for determining the tidal volume of a patient as defined in claim 7 wherein said first flow sensor senses the gases exhaled by a patient during the expiratory cycle and said second sensor senses the flow of gas in said fresh gas tubing during the expiratory cycle.

9. The system for determining the tidal volume of a patient as defined in claim 8 wherein said processor includes means for subtracting the flow of gas determined by said second sensor from the flow of gas determined by said first flow sensor and further includes means for integrating the difference with respect to a known period of time.

10. The system for determining the tidal volume of a patient as defined in claim 9 wherein said known period of time is the time of the expiratory cycle.

11. The system for determining the tidal volume of a patient undergoing anesthesia as defined in claim 10 wherein said breathing means is a ventilator.

12. A system for determining the tidal volume of gas provided to a patient undergoing anesthesia, said system comprising a breathing means, including a source of anesthesia, to supply breaths to a patient during an inspiratory cycle and to allow a patient to exhale during an expiratory cycle, a patient breathing circuit having a main delivery tube having a distal end for connection to the breathing means and a proximal end for connection to a patient connector in communication with a patient, the main delivery tube communicating between said breathing means and a patient, a source of fresh gas, a tubing for delivering the fresh gas from said source of fresh gas to the patient connector for delivery to a patient, means to determine the flow of gas within said main delivery tube, means to determine the flow of fresh gas in said tubing during said inspiratory cycle, a processor for receiving signals from said means to determine the fresh gas flow in said tubing and the flow of gas in said main delivery tube to provide an accurate measurement of the volume of gas delivered to a patient.

13. The system for determining the tidal volume of gas provided to a patient undergoing anesthesia as defined in claim 12 wherein said processor includes means for adding the flow of gas determined by said means to determine the flow in said main delivery tube and the flow of gas determined by said means to determine the flow of fresh gas in said tubing during the inspiratory cycle.

14. The system for determining the tidal volume of gas provided to a patient as defined in claim 12 wherein said means to determine the flow in said main delivery tube comprises a flow sensor located in the distal end of said main delivery tube.

* * * * *